US012642557B2

(12) United States Patent
Harvey et al.

(10) Patent No.: US 12,642,557 B2
(45) Date of Patent: *Jun. 2, 2026

(54) METHOD AND SYSTEM FOR INSTALLING A SENSOR IN A BODY

(71) Applicant: MY01 IP HOLDINGS INC., Montreal (CA)

(72) Inventors: Edward J. Harvey, Montreal (CA); Charles Allan, Montreal (CA); Blake Lariviere, Surrey (CA)

( * ) Notice: Subject to any disclaimer, the term of this patent is extended or adjusted under 35 U.S.C. 154(b) by 347 days.

This patent is subject to a terminal disclaimer.

(21) Appl. No.: 18/189,503

(22) Filed: Mar. 24, 2023

(65) Prior Publication Data

US 2023/0293203 A1 Sep. 21, 2023

Related U.S. Application Data

(63) Continuation of application No. 16/493,950, filed as application No. PCT/IB2018/051712 on Mar. 14, 2018, now Pat. No. 11,633,212.

(60) Provisional application No. 62/471,086, filed on Mar. 14, 2017.

(51) Int. Cl.
*A61B 17/34* (2006.01)
*A61B 5/00* (2006.01)

(52) U.S. Cl.
CPC .......... *A61B 17/3468* (2013.01); *A61B 5/686* (2013.01); *A61B 2560/063* (2013.01)

(58) Field of Classification Search
CPC ................ A61B 17/3468; A61B 5/686; A61B 2560/063
See application file for complete search history.

(56) References Cited

U.S. PATENT DOCUMENTS

| | | |
|---|---|---|
| 7,920,906 B2 | 4/2011 | Goode et al. |
| 9,161,775 B1 | 10/2015 | Katra et al. |
| 2005/0251237 A1 | 11/2005 | Kuzma et al. |
| 2007/0021736 A1 | 1/2007 | Johnson |
| 2007/0293912 A1 | 12/2007 | Cowan et al. |
| 2008/0057779 A1 | 3/2008 | Mastrototaro et al. |
| 2010/0081875 A1 | 4/2010 | Fowler et al. |
| 2012/0143029 A1 | 6/2012 | Silverstein et al. |

*Primary Examiner* — Joseph M Dietrich
(74) *Attorney, Agent, or Firm* — Anglehart et al.

(57) ABSTRACT

A system for installing a sensor, the system comprising: a puncture device for puncturing a skin of a body comprising: a casing defining a cavity; an elongated member a sharp end; and a sensor assembly for measuring data about the body, the sensor assembly comprising: a sensing unit comprising a sensor for measuring the data and being engageable with the elongated member; a data unit for collecting the data, the data collecting unit being receivable within the cavity of the casing; and a communication cable extending between the sensing unit and the data collecting unit for transmitting the data to the data unit, the sensor assembly being removably securable to the puncture device by inserting the data unit in the cavity of the casing and engaging together the sensing unit and the elongated member, the communication cable being tensed when the sensor assembly is secured to the puncture device.

15 Claims, 9 Drawing Sheets

| Securing the sensor assembly 300 to the puncture device 200 |
| --- |

402

| Inserting the puncturing end 208 of the elongated body 202 having the sensing unit 302 removably secured thereto under the skin of the body |
| --- |

404

| Removing the housing 316 of the data collecting unit 314 from the cavity 240 of the casing 228 |
| --- |

406

| Removing the elongated member 202 from under the skin of the body |
| --- |

408

METHOD AND SYSTEM FOR INSTALLING A SENSOR IN A BODY

TECHNICAL FIELD

The present invention relates to the field of sensors and more particularly to a method and system for installing a sensor in a body.

BACKGROUND

Implantable biocompatible sensors are adapted to be inserted under a subject's skin near organs in order to measure and collect data of the subject body. Implantable biocompatible sensors have undergone extensive improvements over the years and find a variety of applications for offering a rapid and accurate way for doctors, nurses and caregivers to monitor subjects with particular medical conditions.

Implantable biocompatible sensors can be adapted to measure and collect a plurality of vital data of the body such as pressure, temperature, pH, blood flow, oxygen saturation and the like. After a compartment injury or compromise, resulting for instance from a trauma from an important collision or impact with the body, the pressure caused by tissue perfusion at the impact point is increased, thus lowering the blood flow and causing a decreased vascularization of certain organs which can create an emergency state for a subject. It is therefore important to constantly measure the body pressure after a collision or serious impact in order to detect any serious problem that could eventually cause serious damage to vital organs.

Nowadays, techniques for implanting a biocompatible sensor require the use of a transducer module, a catheter and a needle. In this configuration, the transducer module is configured to process the sensor signal received from the sensor which was implanted under the skin using the needle associated to the catheter. However, the main disadvantage of such a technique is that many components are needed in order to implant the sensor under the skin.

There is therefore a need for an improved method and system for installing a sensor in a body.

SUMMARY

According to a first broad aspect, there is provided a system for installing a sensor in a body, the system comprising: a puncture device for puncturing a skin of a body comprising: a casing defining a cavity; an elongated member projecting from the casing and comprising a sharp end for puncturing the skin; and a sensor assembly for measuring and collecting data about the body, the sensor assembly comprising: a sensing unit comprising a sensor body and a sensor contained in the sensor body, the sensor for measuring the data and the sensor body being engageable with the elongated member; a data collecting unit for collecting and storing the data, the data collecting unit being receivable within the cavity of the casing; and a communication cable extending between the sensing unit and the data collecting unit for transmitting the data measured by the sensor to the data collecting unit; wherein the sensor assembly is removably securable to the puncture device by inserting the data collecting unit in the cavity of the casing and engaging together the sensing unit and the elongated member, and wherein the communication cable is tensed when the sensor assembly is removably secured to the puncture device.

In one embodiment, the puncture device further comprises an anchoring pin projecting therefrom and the sensor body is provided with an anchoring recess for receiving the anchoring pin, the sensing unit and the elongated member being engageable together by inserting the anchoring pin into the anchoring recess.

In one embodiment, the anchoring pin is adjacent to the sharp end of the elongated member.

In one embodiment, the elongated member is provided with a sensing unit receiving recess for receiving at least a portion of the sensing unit therein, the anchoring pin extending within the sensing unit receiving recess.

In one embodiment, the communication cable is stretchable.

In one embodiment, the puncture device further comprises at least one resilient arm projecting within the cavity.

In one embodiment, the at least one resilient arm each projects from a wall adjacent to the elongated member.

In one embodiment, the casing is further provided with an aperture emerging in the cavity for disengaging the data collecting unit from the cavity.

In one embodiment, the casing is further provided with at least one grip each protruding from an external face thereof.

According to a second broad aspect, there is provided a puncture device for puncturing a skin of a body, the puncture device comprising: a casing defining a cavity for receiving therein a data collecting unit of a sensor assembly, the sensor assembly further comprising a sensing unit for measuring data about a body and a communication cable extending between the sensing unit and the data collecting unit; an elongated member projecting from the casing and comprising a sharp end for puncturing the skin; and an anchoring pin projecting from the elongated member adjacent to the sharp end, the anchoring pin being insertable into a recess formed into the sensing unit, wherein the sensor assembly is removably securable to the puncture device by inserting the data collecting unit in the cavity of the casing and inserting the anchoring pin into the recess of the sensing unit, and wherein the communication cable is tensed when the sensor assembly is removably secured to the puncture device.

In one embodiment, the anchoring pin is adjacent to the sharp end of the elongated member.

In one embodiment, the elongated member is provided with a receiving recess for receiving at least a portion of the sensing unit therein, the anchoring pin extending within the receiving recess.

In one embodiment, the puncture device further comprises at least one resilient arm projecting within the cavity.

In one embodiment, the at least one resilient arm each projects from a wall adjacent to the elongated member.

In one embodiment, the casing is further provided with an aperture emerging in the cavity for disengaging the data collecting unit from the cavity.

In one embodiment, the casing is further provided with at least one grip each protruding from an external face thereof.

According to another broad aspect, there is provided a sensor assembly for measuring and collecting data about the body, the sensor assembly comprising: a sensing unit comprising a sensor body and a sensor contained in the sensor body, the sensing unit being at least partially insertable under a skin of a body, the sensor for measuring the data and the sensor body being engageable with the elongated member, and the sensor body defining an anchoring recess; a data collecting unit for collecting and storing the data, the data collecting unit being receivable within the cavity of the casing; and a communication cable extending between the sensing unit and the data collecting unit for transmitting the data measured by the sensor to the data collecting unit; wherein the sensor assembly is removably securable to a puncture device comprising a casing defining a cavity, an elongated member projecting from the casing and comprising a sharp end for puncturing the skin and an anchoring pin projecting from the elongated member adjacent to the sharp end, wherein the sensor assembly is removably securable to the puncture device by inserting the data collecting unit in the cavity of the casing and inserting the anchoring pin into the recess of the sensing unit, and wherein the communication cable is tensed when the sensor assembly is removably secured to the puncture device.

In one embodiment, the communication cable is stretchable.

According to a further broad aspect, there is provided a method for installing a sensor in a body, the method comprising: providing a puncture device comprising a casing defining a cavity and an elongated member projecting from the casing and comprising a sharp end for puncturing the skin; providing a sensor assembly for measuring and collecting data about the body, the sensor assembly comprising a sensing unit comprising a sensor body and a sensor contained in the sensor body, a data collecting unit for collecting and storing the data and a communication cable extending between the sensing unit and the data collecting unit for transmitting the data measured by the sensor to the data collecting unit, the sensor body being engageable with the elongated member; removably securing the sensor assembly to the puncture device by engaging together the sensor body and the elongated member and inserting the data collecting unit into the cavity of the casing; inserting at least a section of the elongated member under the skin of the body by puncturing the skin with the sharp end of the elongated member; removing the data collecting unit from the cavity of the casing, thereby disengaging the sensor assembly from the puncture device; and removing the elongated member from under the skin of the body, thereby letting the sensing unit under the skin of the body.

In one embodiment, the elongated member is provided with an anchoring pin projecting therefrom and the sensor body is provided with an anchoring recess for receiving the anchoring pin, the step of engaging together the sensor body and the elongated member comprising inserting the anchoring pin into the anchoring recess.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION

Figure 1:
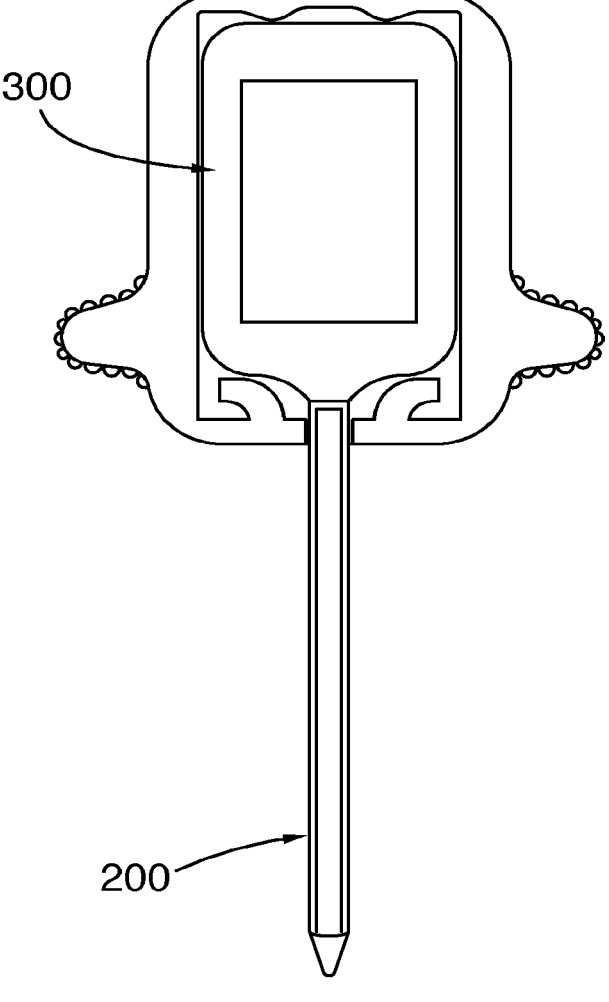
FIG. 1 is a top view of a system for installing a sensor comprising a puncture device and a sensor assembly, in accordance with an embodiment.

With reference to FIG. 1, there is shown a system 100 for installing a sensor under the skin of a body. In the illustrated embodiment, the system 100 comprises a puncture device 200 and a sensor assembly 300.

It should be understood that installing the sensor under the skin of the body includes installing the sensor subcutaneously, but could instead include installing the sensor intramuscularly, intracompartmentaly or elsewhere within the body.

FIGS. 2 to 5 illustrate the puncture device 200 comprising an elongated member 202 and a casing 228 and configured to puncture a body's skin for installing a sensor.

Figure 2:
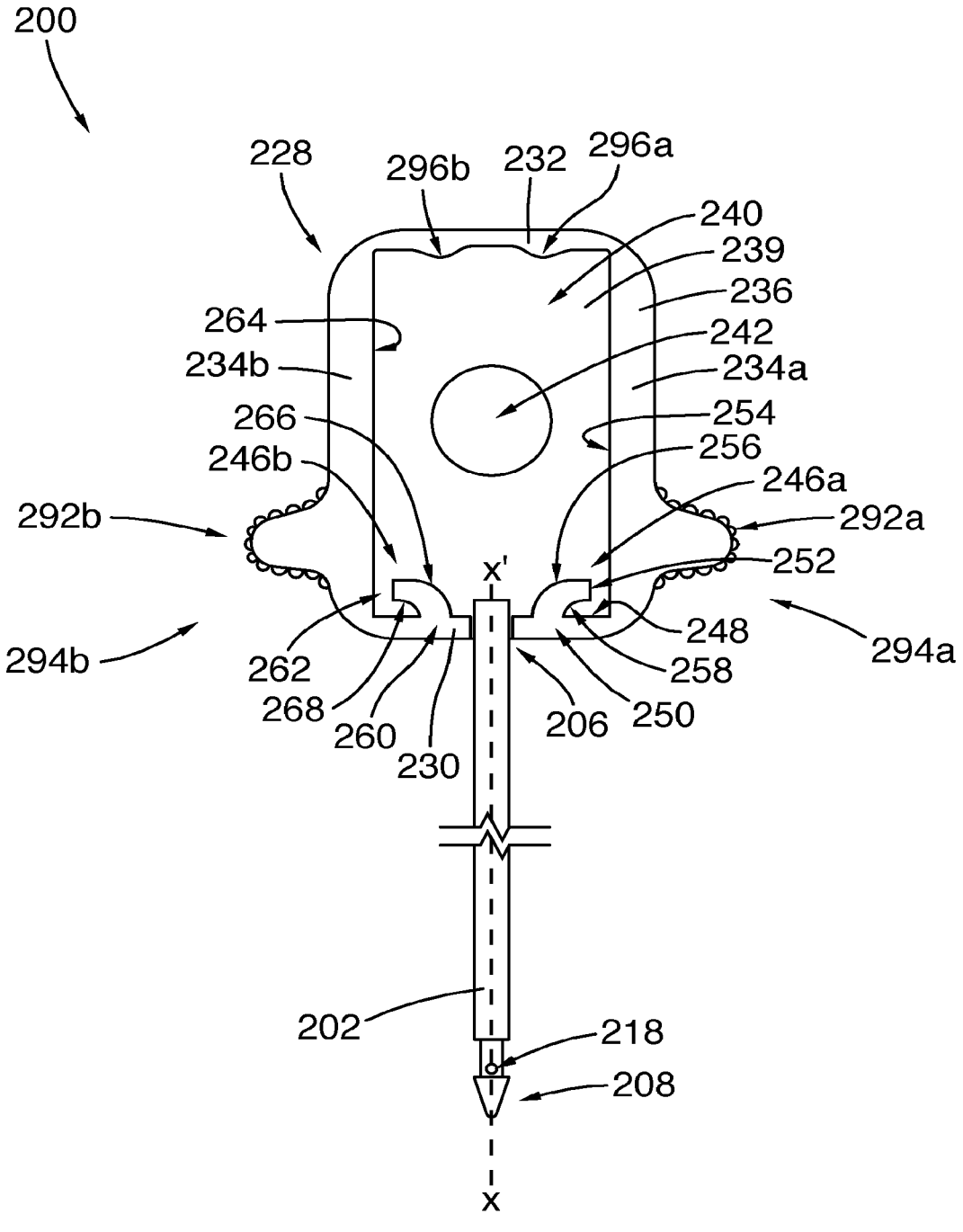
FIG. 2 is a top view of the puncture device of FIG. 1 according to a first embodiment, without the sensor assembly installed thereon.
Figure 3:
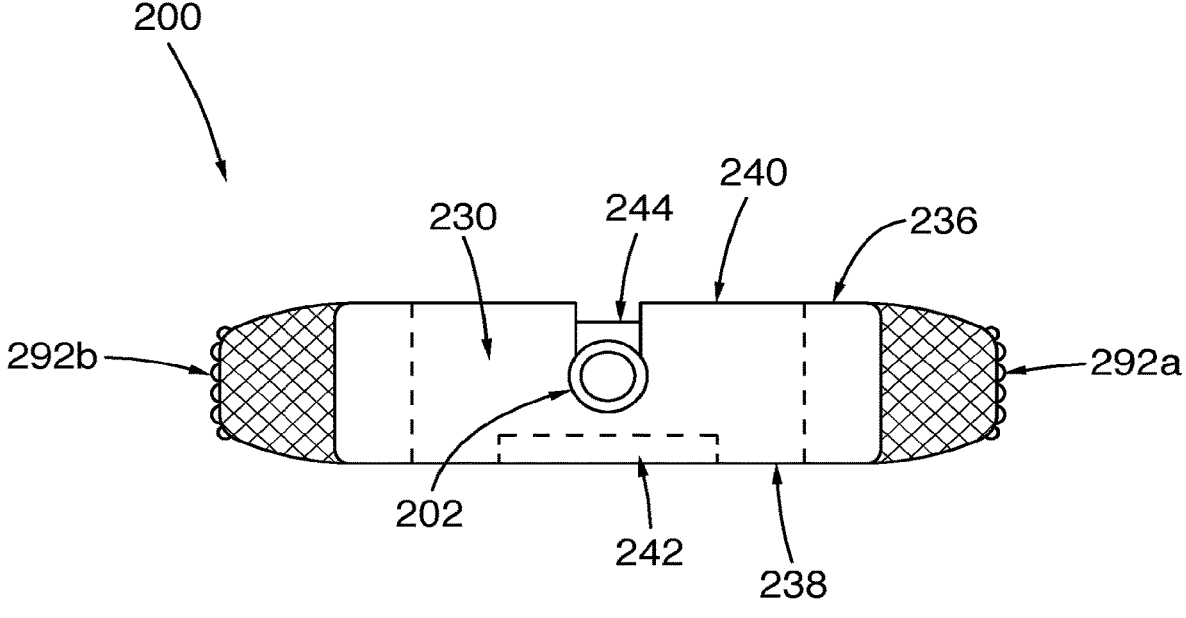
FIG. 3 is a front view of the puncture device of FIG. 2.

The elongated member 202 is adapted to penetrate under a body's skin for installing a sensor. The elongated member 202 has a generally cylindrical shape, comprises an external surface 204 and extends between a connecting end 206 and a puncturing end 208 along a longitudinal axis X-X', as shown in FIG. 2. The connecting end 206 is adapted to be received in an aperture of the casing 228 and secured therein, as described below. In one embodiment, the connecting end 206 may be removably secured to the casing 228 so that different elongated members be secured to a same casing 228. Alternatively, the connecting end 206 may be fixedly secured to the casing 228. The puncturing end 208 has a sharp or pointed shape so as to be able to penetrate under a body's skin.

Adjacent to the puncturing end 208, the elongated member 202 comprises a recess 216 defined by a first inclined face 210, a second inclined face 212 and a bottom face 214 extending therebetween. The recess 216 extends transversally the entire diameter of the elongated member 202 from left to right, and along a given section of the diameter of the elongated member from top to bottom.

The elongated member 202 further comprises an anchoring pin 218 for securing a sensor body of the sensor assembly 300 thereon, as described below. The anchoring pin 218 protrudes upwardly from the bottom face 214 within the recess 216 towards the first inclined face 210. In the embodiment shown in FIG. 5, the anchoring pin 218 comprises a first angled surface 220, a second angled surface 222 and an abutment surface 224. The first angled surface 220 faces the first inclined face 210 and extends upwardly from the bottom face 214 of the recess 216. The second angled surface 222 faces the second inclined face 212 and extends upwardly from the bottom face 214 of the recess 216. The abutment surface 224 extends from the first angled surface 220 to the second angled surface 222 away from the bottom face 214. The anchoring pin 218 may have any adequate cross-section shape. For example, its cross-section may be circular, square, rectangular or the like.

In one embodiment, the puncturing end 208 defines a sharp pointed end 226. In one embodiment, the angle α between the lateral surface 227 defining the sharp pointed end 226 and the longitudinal axis X-X' is comprised between about 10 degrees and about 80 degrees. In one embodiment, the angle β between the first inclined face 210 and the bottom face 214 is comprised between about 30 degrees and about 90 degrees. In one embodiment, the angle θ between the bottom face 214 and the first angled surface 220 of the anchoring pin 218 is comprised between about 30 degrees and about 90 degrees. In one embodiment, the angle γ between the second angled surface 222 of the anchoring pin 218 and the bottom face 214 of the recess 216 is comprised between about 30 degrees and about 90 degrees.

While in the above embodiment the elongated member 202 is provided with a recess 216 comprising an anchoring pin 218, it should be understood that the recess 216 may be omitted and that the anchoring pin 218 may project directly from the external surface 204 of the elongated member 202.

In one embodiment, the diameter of the elongated member 202 varies between 0.5 and 10 millimeters. In one embodiment, the distance A between the sharp pointed end 226 and the external surface 204 having a constant diameter is comprised between about 2 millimeters and about 15 millimeters. In one embodiment, the depth B of the recess 216 between the external surface 204 and the bottom face 214 is comprised between about 0.7 millimeter and about 7 millimeters. In one embodiment, the height of the anchoring pin 218 is less than the depth B of the recess 216. In one embodiment, the longitudinal length C of the abutment surface 224 of the anchoring pin 218 is comprised between about 1 millimeter and about 5 millimeters.

It will be appreciated that according to the ranges provided above, the depth B may be greater than the radius of the elongated member 202.

Figure 5:
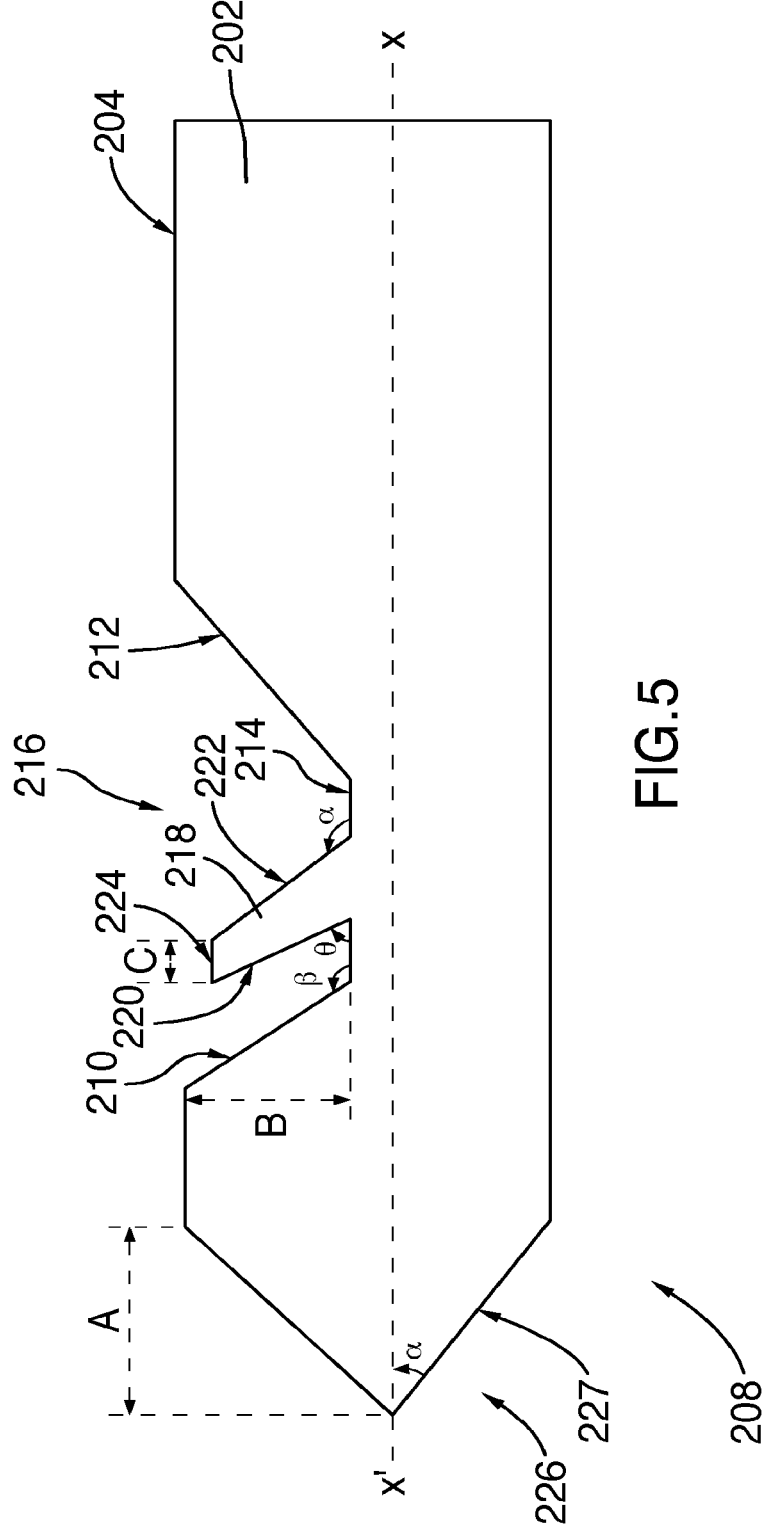
FIG. 5 is an enlarged right side cross-sectional view of the puncturing end of the elongated member comprising an anchoring pin.

Although in the illustrated embodiment of FIG. 5, the recess 216 extends laterally through the entire diameter of the elongated member 202, other configurations are possible. For example, the width of the recess 216 may be less than the diameter of the elongated member 202.

In the illustrated embodiment, the casing 228 has a generally rectangular shape and is configured to receive a data collecting unit comprised in the sensor assembly 300. The casing 228 comprises a front wall 230, a back wall 232 and side walls 234a and 234b. The casing 228 extends between a front face 236 which is formed of the front face of the walls 230, 232, 234a and 234b, and a rear face 238 which is formed of a rear wall 239 and the rear face of the walls 230, 232, 234a and 234b. The walls 230, 232, 234a and 234b define a main cavity 240 which extends from the front face 236 towards the rear wall 239. The rear wall 239 is provided with an opening 242. In the illustrated embodiment, the opening 242 is circular and located substantially at the center of the main cavity 240.

Although in the illustrated embodiment, the main cavity 240 has a generally rectangular shape, it should be understood that other configurations may be possible as long as the data collecting unit of the sensor assembly may be removably received therein. For instance, the main cavity 240 could have a circular or square shape.

The front wall 230 comprises an aperture 244 which extends from the front face thereof through the entire thickness thereof. Optionally, the aperture 244 may be symmetrically positioned between the side walls 234a and 234b. The aperture 244 is shaped and sized for receiving therein the connecting end 206 of the elongated member 202. In one embodiment, the width of the aperture 244 substantially correspond to the diameter of the elongated member 202.

Although in the illustrated embodiment, the aperture 244 has a U-shape, it should be understood that other configurations are possible as long as the elongated member 202 can be received and secured in the aperture 244. For instance, the aperture 244 could have a rectangular shape or any other shape matching that of the connecting end 206 of the elongated member 202.

In one embodiment, the casing 228 further comprises a pair of resilient members or arms 246a and 246b which each project inwardly from the internal surface 248 of the front wall 230 within the cavity 240. The resilient members 246a and 246b each have a curved shape and each extend towards the side walls 234a and 234b, respectively. Optionally, the resilient members 246a and 246b may be disposed symmetrically relative the aperture 244.

The resilient members 246a and 246b have a generally semi-circular shape and are used to removably secure the data collecting unit of the sensor assembly 300 within the main cavity 240. The resilient members 246a and 246b are designed so as to be elastically deformable upon application of a force thereon as described below. The resilient member 246a extends in a circular fashion between a first end 250 secured to the internal surface 248 of the front wall 230 and a second end 252 which substantially faces the internal surface 254 of the side wall 234a and is located away from the internal surface 254. The resilient member 246a extends along the axis X-X' between an abutment face 256 which substantially faces the back wall 232 of the casing 228 and an opposite face 258 which substantially faces the front wall 230.

While the resilient member 246a projects towards the side wall 234a, it should be understood that the resilient member 246b, being a mirror image of the resilient member 246a, projects towards the side wall 234b, symmetrically relative the aperture 244 of the front wall 230. Therefore, the resilient member 246b extends in a circular fashion between a first end 260 secured to the internal surface 248 of the front wall 230 and a second end 262 which substantially faces the internal surface 264 of the side wall 234b and is located away from the internal surface 264. The resilient member 246b extends along the axis X-X' between an abutment face 266 which substantially faces the back wall 232 of the casing 228 and an opposite face 268 which substantially faces the front wall 230.

The resilient members 246a and 246b are each movable between two configurations/states, i.e. a rest configuration/state and a contracted configuration/state, upon application of a force thereon thanks to their elastically deformation property. When in the rest configuration, no force is applied on the resilient member 246a, 246b and the end 252, 262 of the resilient member 246a, 246b, respectively, is located at a first distance from the internal surface 248 of the front wall 230. By applying a force on the section of the abutting face 256, 266 adjacent the end 252, 262 towards the front wall 230, the end 252, 262 of the resilient member 246a, 246b moves towards the front wall 230 so that the distance between the end 252, 262 and the front wall 230 decreases. The resilient member 246a, 246b is then in the contracted configuration. When the force exerted on the abutting face 256, 266 of the resilient member 246a, 246b is released, the resilient member 246a, 246b goes back to its rest configuration.

Although in the illustrated embodiment, the casing 228 comprises the resilient members 246a and 246b being mirror images of one another and located symmetrically relative the aperture 244, it should be understood that other configurations may be possible. For example, the resilient members 246a and 246b may be positioned asymmetrically relative to the aperture 244. While the resilient members 246a and 246b each project inwardly from the front wall 230, it should be understood that the resilient members 246a and 246b may project from the back wall 232. It should also be understood that the number and position of the resilient members may vary as long as the casing 228 is provided with at least one resilient member which project inwardly from the front or back wall 230, 232. For instance, the casing 228 could be provided with a single resilient member projecting inwardly from the front wall 230. In another example, the casing 228 could be provided with a single resilient member projecting inwardly from the back wall 232. In another example, the casing 228 could comprise more than two resilient members projecting from the front wall 230 and/or the back wall 232.

It should also be understood that the shape of a resilient member may vary as long as at least a portion of the resilient member is elastically deformable for removably securing the data collecting unit of the sensor assembly 300 within the main cavity 240, as described below. It should also be understood that any adequate means for removably securing the data collecting unit to the casing 228 may be used. For example, a spring may be secured the front wall 230 or the back wall 232 to removably secure the data collecting unit within the cavity 240.

Figure 4:
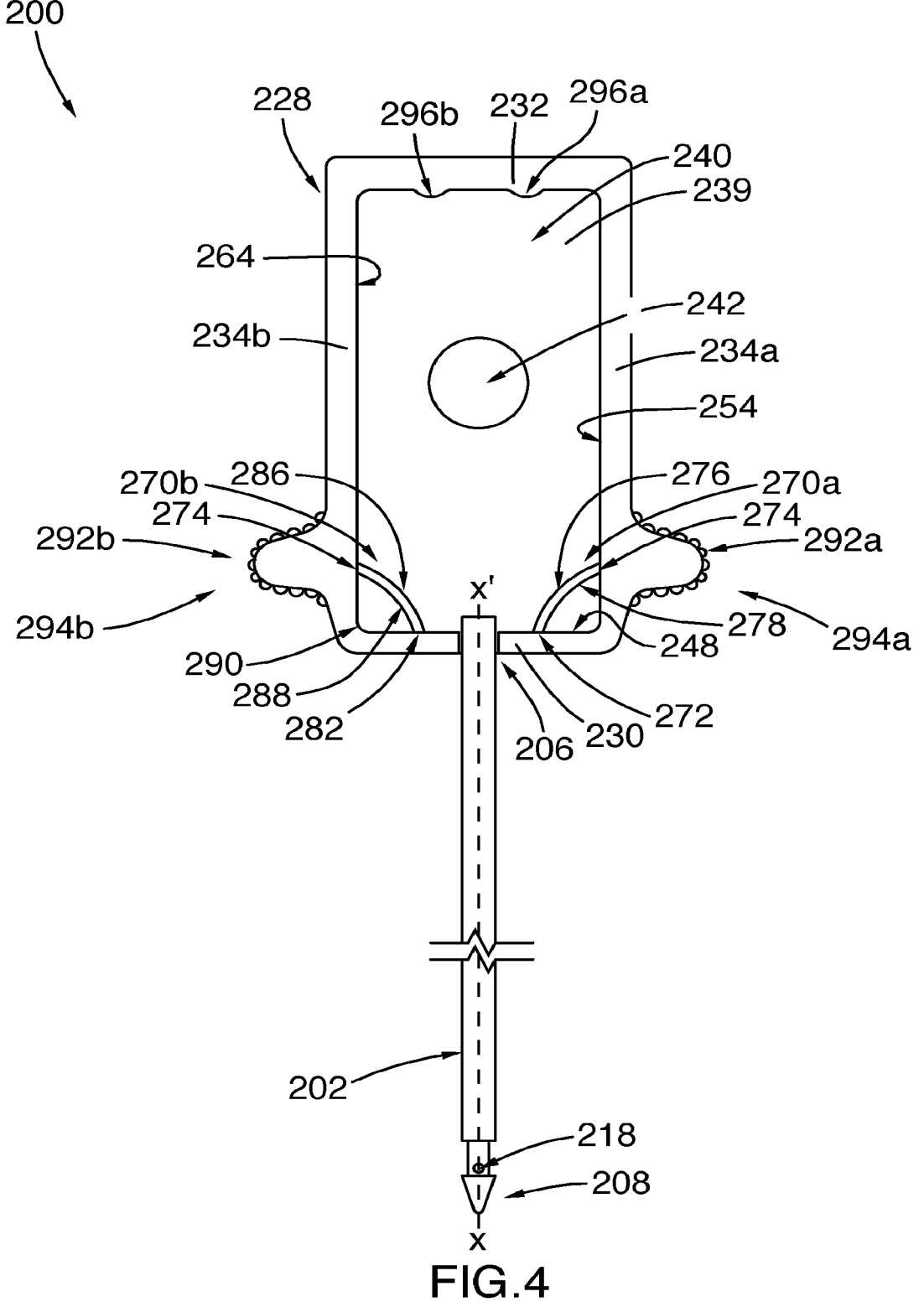
FIG. 4 is a top view of a puncture device according to a second embodiment, without the sensor assembly installed thereon.

FIG. 4 illustrates an exemplary alternative design for a resilient member. In this embodiment the casing 228 comprises two resilient members 270a and 270b each connected between the front wall 230 and the side wall 234a, 234b, respectively.

The resilient member 270a has a generally semi-circular shape and is used to removably secure the data collecting unit of the sensor assembly 300 within the main cavity 240. The resilient member 270a is designed so that at least a section thereof be elastically deformable upon application of a force thereon as described below. The resilient member 270a extends longitudinally in a circular fashion between a first end 272 secured to the internal surface 248 of the front wall 230 and a second end 274 secured to the internal surface 254 of the side wall 234a. The resilient member 270a also extends transversally between an abutment face 276 which substantially faces the back wall 232 and the side wall 234b, and an opposite face 278 which substantially faces the junction corner 280 between the front wall 230 and the side wall 234a.

Similarly, the resilient member 270b has a generally semi-circular shape and is used to removably secure the data collecting unit of the sensor assembly 300 within the main cavity 240. The resilient member 270b is designed so that at least a section thereof be elastically deformable upon application of a force thereon as described below. The resilient member 270b extends longitudinally in a circular fashion between a first end 282 secured to the internal face 248 of the front wall 230 and a second end 284 secured to the internal face 264 of the side wall 234b. The resilient member 270b also extends transversally between an abutment face 286 which substantially faces the back wall 232 and the side wall 234a and an opposite face 288 which substantially faces the junction corner 290 between the front wall 230 and the side wall 234b.

The resilient member 270a, 270b is movable between two configurations, i.e. a rest configuration and a contracted configuration, upon application of a force thereon thanks to their elastically deformation property. When in the rest position, no force is applied on the resilient member 270a, 270b and the central section of the resilient member 270a, 270b is located at a first distance from the junction corner 280, 290, respectively. By applying a force on the abutting face 276, 286 towards the front wall 230, the side wall 234a, 234b and/or the junction corner 280, 290, the central section of the resilient member 270a, 270b moves towards the junction corner 280, 290, respectively, so that the distance between the central section of the resilient member 270a, 270b and the junction corner 280, 290 decreases. The resilient member 270a, 270b is then in the contracted configuration. When the force exerted on the abutting face 276, 286 of the resilient member 270a, 270b is released, the resilient member 270a, 270b goes back to its rest configuration.

In one embodiment, the casing 228 is further provided with two grips 292a and 292b for helping a user manipulate the puncture device 200. The grip 292a has the shape of a curved protrusion and extends outwardly from the side wall 234a adjacent to first end 294a of the side wall 234a. Similarly, the grip 292b has the shape of a curved protrusion and extends outwardly from the side wall 234b adjacent to the end 294b of the side wall 234b. In the illustrated embodiment, the grips 292a and 292b each comprise a crenelated surface adapted to create an improved grip for a user during manipulation of the puncture device 200.

Although in the illustrated embodiment, the grip 292a, 292b is located adjacent a first end 294a, 294b of the casing 228 and has the shape of a curved protrusion, it should be understood that other configurations may be possible and the number, shape and/or position of the grips may vary. For instance, the grip 292a, 292b could be located at a different location on the external surface of the side wall 234a, 234b, respectively, between the front and back walls 230 and 232. Moreover, the grips 292a, 292b could alternatively have a rectangular shaped protrusion for optimizing grasping of the puncture device 200 by a user.

In an alternative embodiment, each side wall 234a, 234b could comprise a plurality of grips for creating a crenellated external surface and improving the grasping and the manipulation by a user. Moreover, the grips 292a and 292b could have the shape of handles, for example.

In one embodiment, the casing 228 comprises a pair of contacting elements 296a and 296b which each protrude inwardly from the back wall 232 within the main cavity 240. In the illustrated embodiment, the contacting elements 296a and 296b are disposed symmetrically relative the aperture 244 of the front wall 230. The contacting elements 296a and 296b have the shape of a curved protrusion and are adapted to abut against a data collecting unit when inserted in the main cavity 240, as described below.

It should be understood that the number, position and/or shape of the contacting elements may vary. For instance, the back wall 232 could have more than two contacting elements 296a and 296b disposed between the side walls 234a and 234b. Moreover, the contacting elements 296a and 296b could have a different shape such as a square or a rectangular shape. The contacting elements 296a and 296b could also project from the side walls 234a or 234b.

Figures 6, 7:
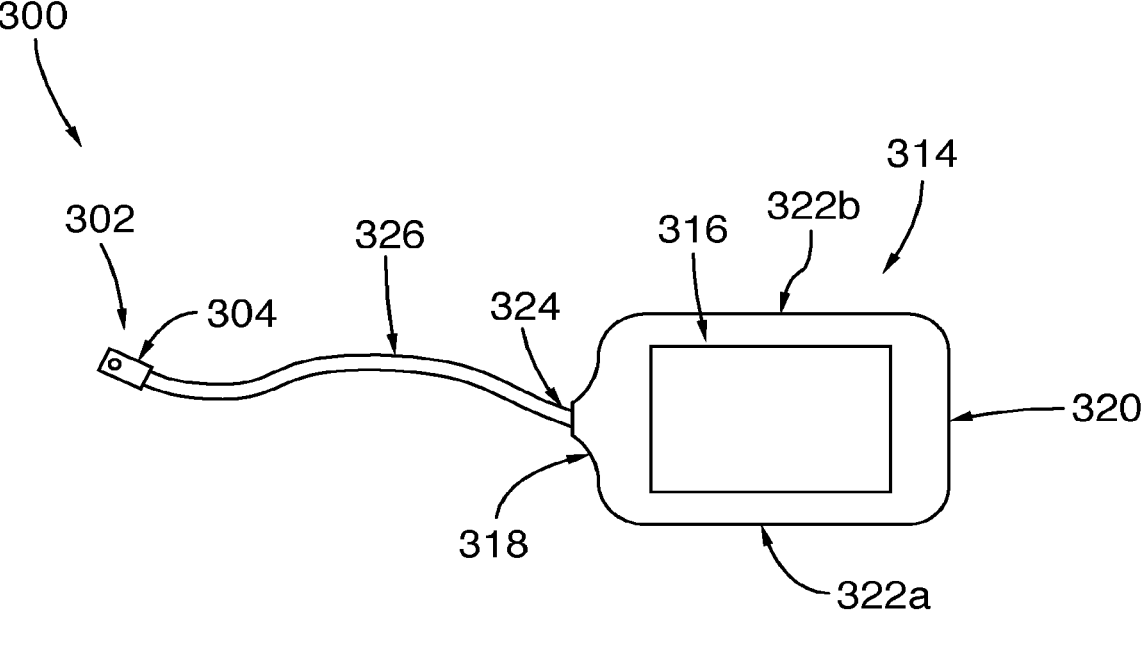
FIG. 6 is a top view of the sensor assembly comprising a sensing unit, communication cable and a data collecting unit.
FIG. 7 is an enlarged right side cross-sectional view of a portion of the sensing unit of FIG. 6 showing the sensor body and a portion of the communication cable.

FIG. 6 illustrates one embodiment of the sensor assembly 300. The sensor assembly 300 comprises a sensing unit 302, a data collecting unit 314 and a communication cable 326 having a first end connected to the sensing unit 302 and a second end connected to the data collecting unit 314. The sensing unit 302 is adapted to measure a parameter or characteristic of a body when inserted under the skill of the body. The data collecting unit 314 is adapted to receive measurement values from the sensing unit 302 via the communication cable 326.

FIG. 7 illustrates one embodiment of the sensing unit 302. In this embodiment, the sensing unit 302 comprises a sensor body 304 and a sensor 306 housed in the sensor body 304. The sensor body 304 has a generally rectangular shape, and is sized to fit in the recess 216 of the elongated member 202. The sensor body 304 comprises a top surface 308 and a bottom surface 310. The recess 312 extends from the bottom surface 310 towards the top surface and is delimited by a first vertical wall 311, a second vertical wall 313 and a horizontal wall 315 extending between the first and second vertical walls 311 and 313. The recess 312 is adapted to receive therein at least a portion of the anchoring pin 218 of the elongated member 202. In the illustrated embodiment of FIG. 7, the top surface 308 of the sensor body 304 is attached to the communication cable 326.

Referring back to FIG. 6, the data collecting unit 314 comprises a housing 316, a processing unit (not shown) and a memory (not shown). The housing 316 comprises a front wall 318, a back wall 320 and a pair of side walls 322a and 322b and is sized and shaped to be inserted and secured within the main cavity 240 of the casing 228. The distance between the front wall 318 and the back wall 320 of the housing 316 is shorter than the distance between the internal surface 248 of front wall 230 and the back wall 232 of the casing 228. The front wall 318 of the housing 316 further comprises an opening 324 for receiving the communication cable 326. In one embodiment, the shape of the housing 316 substantially matches that of the main cavity 240.

The processing unit is configured for receiving measurement values transmitted by the sensor 306 via the communication cable 326 and storing the received measurement values into the memory. In one embodiment, the data collecting unit 314 further comprises a display unit for displaying data thereon. For example, the measurement values received by the processing unit may be displayed to a user. In the same or another embodiment, the data collecting unit 314 comprises wireless communication means for wirelessly transmitting data such as the measurement values.

The communication cable 326 is adapted to connect the sensor 306 to the data collecting unit 314. In one embodiment, the communication cable 326 may be extensible. In another embodiment, the communication cable 326 may be inextensible.

Figure 8:
FIG. 8 is a block diagram of a method for installing a sensor.
Figure 8:
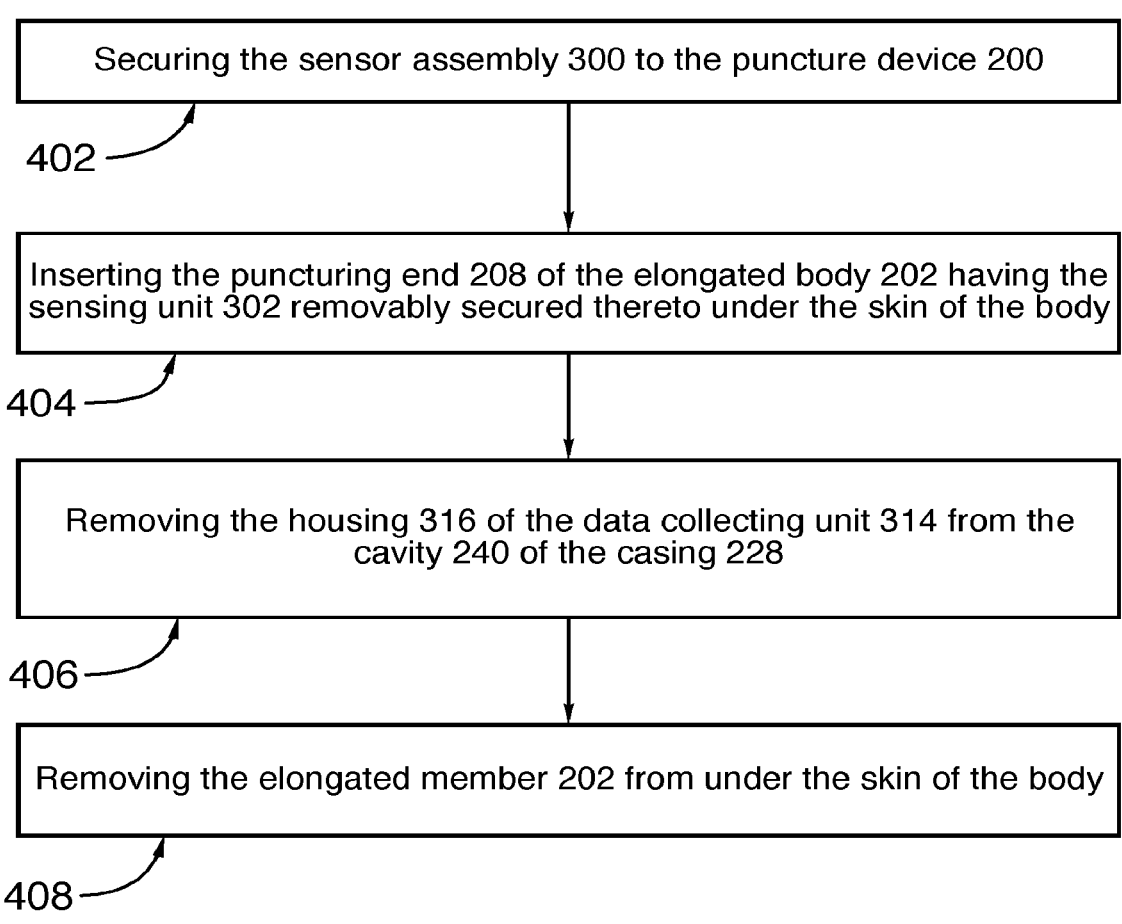

FIG. 8 describes a method 400 for installing the sensing unit 302 under a body's skin using the puncture device 200.

The first step 402 consists in removably securing the sensor assembly 300 to the puncture device 200 so that the data collecting unit 314 be received within the main cavity 240 and the sensing unit 302 be removably secured to the anchoring pin 218.

Figure 9:
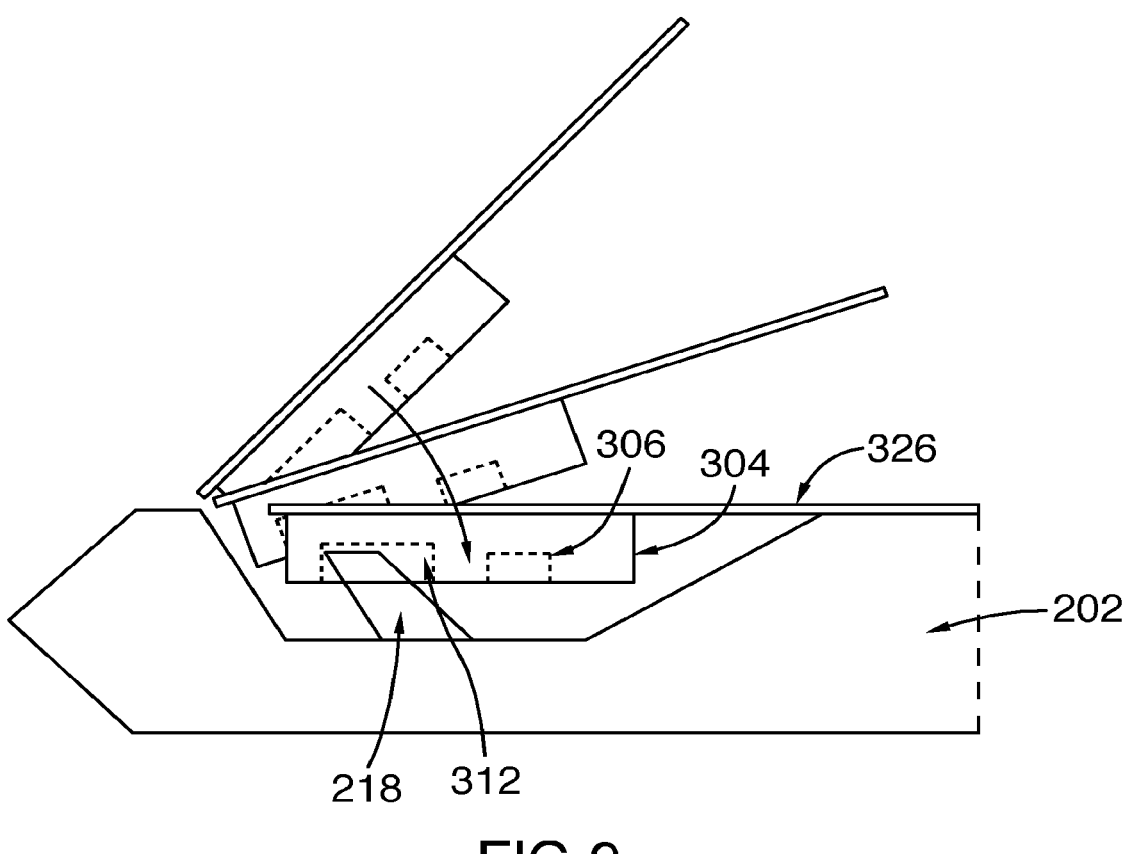
FIG. 9 is an enlarged right side cross-sectional view of the puncturing end of the elongated member showing the insertion of the anchoring pin of the elongated member in the recess of a sensor body.
Figure 10:
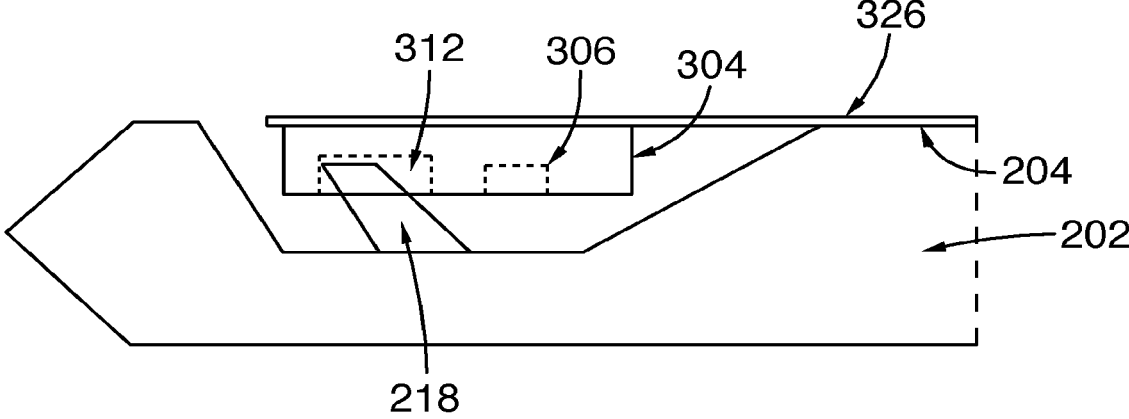
FIG. 10 is an enlarged right side cross-sectional view of the puncturing end of the elongated member having the sensor body installed on the anchoring pin.

In one embodiment, the anchoring pin 218 of the elongated member 202 is first inserted in the recess 312 of the sensor body 304 by abutting the first angled surface 220 and the abutment surface 224 against the first vertical wall 311 and the horizontal wall 315, respectively, as shown in FIG. 9. As the anchoring pin 218 is removably inserted into the recess 312, the housing 316 of the data collecting unit 314 is subsequently inserted in the main cavity 240 of the casing 228. A force is therefore exerted by the sensing unit 302 towards the data collecting unit 314, as the communication cable 326 is longitudinally pulled over the elongated member 202 towards the data collecting unit 314, thanks to the first angled surface 220 abutting against the first vertical wall 311. The data collecting unit 314 is inserted in the main cavity 240 by abutting the front wall 318 of the housing 316 against the resilient members 246a and 246b of the casing 228 and exerting the force on the housing 316 towards the resilient members 246a and 246b to contract them. The resilient members 246a and 246b are therefore moved from their rest configuration to their contracted configuration as they undergo elastic deformation due to the force exerted thereon by the housing 316 of the data collecting unit 314. When the resilient members 246a and 246b are in their contracted configuration, the housing 316 of the data collecting unit 314 is lowered and positioned into the main cavity 240. The force exerted on the housing 316 is then released and the resilient members 246a and 246b are then in an intermediary configuration that is between the rest configuration and the contracted configuration. When in the intermediary configuration, the resilient members 246a and 246b exert a force directed towards the back wall 232 of the casing 228 on the front wall 318 of the housing 316 of the data collecting unit 314. The back wall 232 of the housing 316 then abuts against the contacting elements 296a and 296b and the housing 316 of the data collecting unit 314 is removably secured into the main cavity 240. Once installed, the sensor assembly 300 is stiff and the communication cable 326 is tensed over the external surface 204 of the elongated member 202 so that the anchoring pin 218 be removably secured into the recess 312 of the sensing unit 302, as best shown in FIG. 10.

It should be understood that the order in which the steps for removably securing the sensor assembly 300 to the puncture device 200 are performed may vary. For example, the front wall 318 of the housing 316 may first be abutted against the resilient members 246a and 246b of the casing 228 and pushed against the resilient members 246a and 246b so that a force be exerted by the housing 316 of the data collecting unit 314 on the resilient members 246a and 246b to contract them. The resilient members 246a and 246b are therefore moved from their rest configuration to their contracted configuration as they undergo elastic deformation due to the force exerted thereon by the housing 316 of the data collecting unit 314. When the resilient members 246a and 246b are in their contracted configuration, the sensing unit 302 is removably secured to the anchoring pin 218 by tensing the communication cable 326 and positioning the anchoring pin 218 into the recess 312 of the sensing unit 302. In this case, a force is exerted on the resilient member 246a and 246b by the housing 316 of the data collecting unit 314 towards the sensing unit 202 as the communication cable 326 is pulled over the elongated member 202 in order to position the recess 312 of the sensor body 304 in registry with the anchoring pin 218. The anchoring pin 218 is then inserted into the recess 312 of the sensing unit 304 by abutting the first angled surface 220 and the abutment surface 224 against the first vertical wall 311 and the horizontal wall 315, respectively. The force exerted on the housing 316 of the data collecting unit 314 is then diminished and the resilient members 246a and 246b are therefore in an intermediary configuration that is between the rest configuration and the contracted configuration. When in the intermediary configuration, the resilient members 246a and 246b exert a force directed towards the back wall 232 of the casing 228 on the front wall 318 of the housing 316 of the data collecting unit 314. The back wall 232 of the housing 316 abuts against the contacting elements 296a and 296b and the housing 316 of the data collecting unit 314 is removably secured into the main cavity 240. The sensor assembly 300 is therefore stiff and the communication cable 326 is tensed over the external surface 204 of the elongated member 202 so that the anchoring pin 218 be removably secured into the recess 312 of the sensing unit 302, as best shown in FIG. 10.

At step 404, the puncturing end 208 of the elongated body 202 having the sensing unit 302 removably secured thereto is inserted under the skin of the body until the sensing unit 302 be positioned at an adequate position under the skin. When the sensing unit 302 is in position under the skin of the body, a portion the communication cable 326 may also be inserted under a body's skin. In this step, the handling of the puncture device 200 may be improved thanks to the grips 292a and 292b located on side walls 234a and 234b respectively.

At step 406, the housing 316 of the data collecting unit 314 is removed from the cavity 240 of the casing 228. In one embodiment, the data collecting unit 314 is removed from the casing 228 by applying an upward force on the housing 316 of the data collecting unit 314 through the opening 242 present in the second face 238 of the casing 228. Once the data collecting unit 314 has been removed from the main cavity 240, the resilient members 246a and 246b are shifted back to their rest configuration. The tension in the communication cable 326 is therefore released and the sensing unit no longer exerts a force on the anchoring pin 228, thereby rendering the anchoring pin 218 disengageable from the recess 312 of the sensor body 304.

At step 408, the elongated member 202 is removed from under the skin of the body. The elongated member 202 is pulled, thereby letting the sensing unit 302 in position under the skin.

Figures 11, 12:
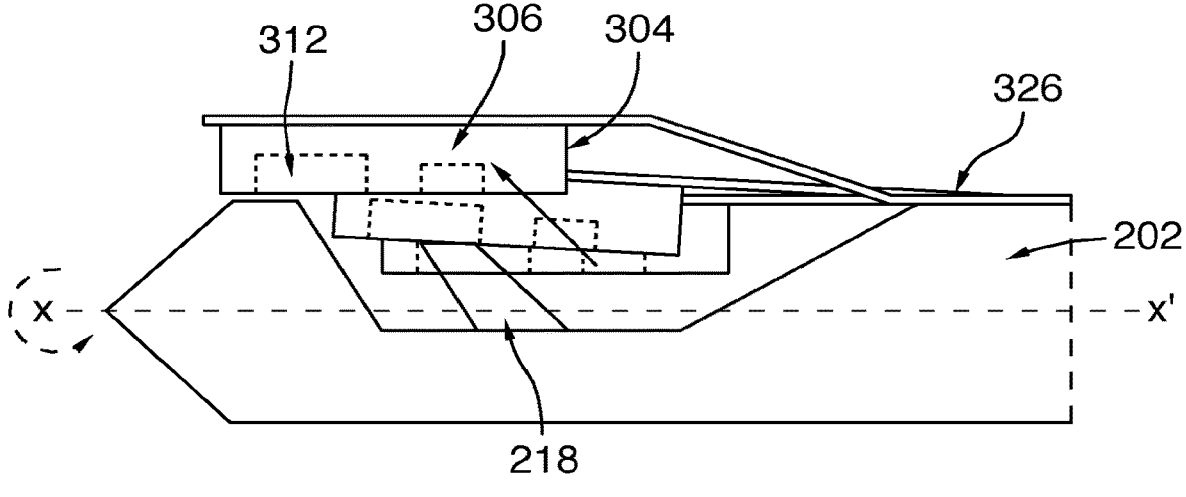
FIG. 11 is an enlarged cross-sectional view of the puncturing end of the elongated member showing the removal of the anchoring pin of the elongated member form the sensor body.
FIG. 12 is an enlarged cross-sectional view of the puncturing end of the elongated member being removed from under the sensing unit.

In one embodiment, the elongated member 202 is rotated before being pulled. By rotating the elongated member 202, as shown in FIG. 12, the anchoring pin 218 is disengaged from the recess 312 of the sensor body 304.

In the same or another embodiment, the anchoring pin 218 is disengaged from the recess 312 of the sensor body 304 by slightly moving the puncturing end 208 of the elongated member 202 away from the sensing unit 302 in order to disengage the tip of the anchoring pin 218 from the recess 312 of the sensor body 304.

In one embodiment, the sensing unit 302 and a portion of the communication cable 326 remain under the skin as the elongated member 202 is pulled.

In another embodiment, only the sensing unit 302 or a portion of the sensing unit 302 remains under the skin as the elongated member 202 is pulled.

In one embodiment the communication cable 326 and/or the data collecting unit 314 are subsequently secured to the body by way of attaching means such as a bandage, a surgical tourniquet, a cuff or the like.

While in the above description, the casing 228 is provided with resilient members 246a and 246b, it should be understood that the resilient members 246a and 246b could be omitted. In this case, the communication cable 326 would be stretchable between a first length, corresponding to a rest position where the communication cable 326 is not pulled and a second length, corresponding to a stretched position where the distance between the sensing unit 302 and the data collecting unit 314 is increased. The housing 316 of the data collecting unit 314 would be shaped and sized to snuggly fit in the casing 228 of the puncture device 200. Therefore, the distance between the front and the back wall 318 and 320 of the housing 316 would be equal to the distance between the front wall 230 and the back wall 232 of the casing 228.

The method for installing a sensor 306 under a body's skin by way of a puncture device comprising no resilient members comprises the following steps.

The sensor assembly 300 is first removably secured to the puncture device comprising no resilient members so that the data collecting unit 314 be received within the main cavity 240 and the sensing unit 302 be removably secured to the anchoring pin 218.

In one embodiment, the anchoring pin 218 of the elongated member 202 is first inserted in the recess 312 of the sensor body 304 by abutting the first angled surface 220 and the abutment surface 224 against the first vertical wall 311 and the horizontal wall 315, respectively, as shown in FIG. 9. As the anchoring pin 218 is removably inserted into the recess 312, the communication cable 326 is stretched and the housing 316 of the data collecting unit 314 is subsequently inserted in the main cavity 240 of the casing 228. The stretching of the communication cable 326 results in a force that is exerted by the sensing unit 302 on the anchoring pin 218 towards the data collecting unit 314. When the housing 316 of the data collecting unit 314 is removably inserted in the main cavity 240 of the casing 228, the communication cable 326 extends through the aperture 244 and has intermediary length that is between the rest length and the stretched length. Once installed, the anchoring pin 218 inserted in the recess 312 of the sensor body 304 is removably secured to the sensor body 304 and forms an anchor point, and the stretched communication cable 326 creates a force between the data collecting unit 314 and the sensing unit 302 for stiffening the sensor assembly 300, as best shown in FIG. 10.

It should be understood that the order in which the sensor assembly 300 is removably secured to the puncture device 200 may vary. For example, data collecting unit 314 may be first inserted into the main cavity 240 of the casing 228. Then the communication cable 326 is stretched and the sensing unit is positioned over the anchoring pin 218 so that the anchoring pin 218 be received in the recess 312 of the sensor body 304. The tension created in the communication cable 326 results in a force that is exerted by the sensing unit 302 on the anchoring pin 218 towards the data collecting unit 314, thereby removably securing the sensing unit 302 to the elongated member 202. When the housing 316 of the data collecting unit 314 is removably inserted in the main cavity 240 of the casing 228, the communication cable 326 extends through the aperture 244 and has intermediary length that is between the rest length and the stretched length. Once installed, the anchoring pin 218 inserted in the recess 312 of the sensor body 304 is removably secured to the sensor body 304 and forms an anchor point, and the stretched communication cable 326 creates a force between the data collecting unit 314 and the sensing unit 302 for stiffening the sensor assembly 300, as best shown in FIG. 10.

The puncturing end 208 of the elongated body 202 having the sensing unit 302 removably secured thereto is subsequently inserted under the skin of the body until the sensing unit 302 be positioned at an adequate position under the skin. When the sensing unit 302 is in position under the skin of the body, a portion the communication cable 326 may also be inserted under a body's skin. In this step, the handling of the puncture device 200 may be improved thanks to the grips 292a and 292b located on side walls 234a and 234b respectively.

The data collecting unit 314 is then removed from the cavity 240 of the casing 228. In one embodiment, the data collecting unit 314 is removed from the casing 228 by applying an upward force on the housing 316 of the data collecting unit 314 through the opening 242 present in the second face 238 of the casing 228. Once the data collecting unit 314 has been removed from the main cavity 240, the tension in the communication cable 326 is released and the sensing unit 302 no longer exerts a force on the anchoring pin 228, thereby rendering the anchoring pin 218 disengageable from the recess 312 of the sensor body 304.

The elongated member 202 is then removed from under the skin of the body. The elongated member 202 is pulled, thereby letting the sensing unit 302 in position under the skin.

In one embodiment, the elongated member 202 is rotated before being pulled. By rotating the elongated member 202, as shown in FIG. 12, the anchoring pin 218 is disengaged from the recess 312 of the sensor body 304.

In the same or another embodiment, the anchoring pin 218 is disengaged from the recess 312 of the sensor body 304 by slightly lowering the puncturing end 208 of the elongated member 202 relative the sensing unit 302 in order to disengage the tip of the anchoring pin 218 from the recess 312 of the sensor body 304.

In one embodiment, the sensing unit 302 and a portion of the communication cable 326 remain under the skin as the elongated member 202 is pulled.

In another embodiment, only the sensing unit 302 or a portion of the sensing unit 302 remains under the skin as the elongated member 202 is pulled.

In one embodiment the communication cable 326 and/or the data collecting unit 314 are subsequently secured to the body by way of attaching means such as a bandage, a surgical tourniquet, a cuff or the like.

In the above embodiments, it should be understood that the length of the communication cable 326, whether stretchable or not, is sized adequately to create a sufficient tension between the sensing unit 302 and the data collecting unit 314 when the first angled surface 220 of the anchoring pin 218 abuts against the first vertical wall 311 of the sensor body 304 and the data collecting unit 314 is received in the casing 228. In the embodiment in which the communication cable 326 is not stretchable, the resilient members 246a and 246b, thanks to their elastic property, are able to be deformed in order to create the necessary tension in the communication cable 326 for installing the sensor assembly 300 on the puncture device 200. In the embodiment in which the resilient members 246a and 246b are omitted, the communication cable 326 is stretchable and has an adequate length for creating the required tension between the sensing unit 302 and the data collecting unit 314 to obtain a stiff sensor assembly 300 adapted to be inserted under the skin of a body.

Although in the illustrated embodiment, the housing 316 of the data collecting unit 314 has a generally rectangular shape adapted to fit in the main cavity 240 of the casing 228, it should be understood that other configurations are possible. For example, depending on the shape of the main cavity 240, the housing 316 would have the same shape.

While in the above description, the anchoring pin 218 is in a longitudinal alignment with the aperture 244 of the casing 228 when the elongated member 202 is connected to the aperture 244, it should be understood that the anchoring pin 218 could be positioned at a different angular position relative the aperture 244.

While the above description refers to an elongated member 202 provided with a an anchoring pin 218 and a sensor body 304 provided with a recess 312 for receiving the anchoring pin 218, it should be understood that the anchoring pin may project from the sensor body 304 and the elongated member 202 may be provided with a pin receiving recess for receiving the anchoring pin of the sensor body 304 in order to removably secure the sensing unit 302 to the elongated member 202.

The embodiments described above are intended to be exemplary only. The scope of the invention is therefore intended to be limited solely by the appended claims.

The invention claimed is:

1. A puncture device for puncturing a skin of a body comprising:

a casing configured to engage with a data collecting unit of a sensor assembly;

an elongated member comprising a puncturing end for puncturing the skin and a connecting end, the elongated member being connected to the casing at the connecting end; and wherein the casing is adapted to be removably securable to the data collecting unit of the sensor assembly and the elongated member is adapted to be removably securable to a sensing unit of the sensor assembly, and wherein a length of the elongated member is sufficient to cause a communication cable of the sensor assembly to be tensed when the casing is removably secured to the data collecting unit of the sensor assembly and the elongated member is removably secured to the sensing unit of the sensor assembly.

2. The puncture device according to claim 1, wherein the casing comprises a cavity for receiving the data collecting unit and at least one resilient arm projecting within the cavity, the at least one resilient arm being configured to elastically deform when the data collecting unit is received in the cavity of the casing.

3. The puncture device according to claim 2, wherein the at least one resilient arm is a spring.

4. The puncture device according to claim 2, wherein the at least one resilient arm has an at least partially curved shape.

5. The puncture device according to claim 1, wherein the connecting end is removably secured to the casing.

6. The puncture device according to claim 1, wherein the connecting end is fixedly secured to the casing.

7. The puncture device according to claim 1, further comprising an anchoring pin projecting from the elongated member to be received in a recess formed in the sensing unit.

8. The puncture device according to claim 7, wherein the anchoring pin extends from the elongated member and is angled relative to the elongated member.

9. The puncture device according to claim 7, wherein the anchoring pin extends from the elongated member and is angled towards the puncturing end.

10. The puncture device according to claim 8, wherein the elongated member further comprises a recess defined therein, the recess extending transversally a diameter of the elongated member.

11. The puncture device according to claim 10, wherein the recess further comprises a first inclined face extending from a bottom face of the recess and a second inclined face extending from the bottom face.

12. A sensor assembly for measuring data about a body, the sensor assembly comprising:

a sensing unit comprising a sensor body and a sensor contained in the sensor body for measuring the data, the sensing unit being at least partially insertable under a skin of the body, the sensing unit being engageable with an elongated member of a puncture device;

a data collecting unit for collecting and storing the data, the data collecting unit being engageable with a casing of the puncture device; and a communication cable extending between the sensing unit and the data collecting unit for transmitting the data measured by the sensor to the data collecting unit; wherein the data collecting unit is adapted to be removably securable to the casing of the puncture device and the sensing unit is adapted to be removably securable to the elongated member, and wherein the communication cable is tensed when the data collecting unit and the casing are removably secured and when the sensing unit and the elongated member are removably secured.

13. An elongated member of a puncture device for puncturing a skin of a body, the elongated member comprising:

a body extending between a puncturing end and a connecting end, the puncturing end being adapted to puncture the skin of the body, the elongated member being connectable to a casing of the puncture device at the connecting end; and an anchoring pin located in a recess of the body, wherein an angle between a longitudinal axis of the body and a surface of the anchoring pin nearest the puncturing end between 30 degrees and 90 degrees.

14. The elongated member according to claim 13, wherein the elongated member further comprises a recess defined therein, the recess extending transversally a diameter of the elongated member.

15. The elongated member according to claim 13, wherein the recess further comprises a first inclined face extending from a bottom face of the recess and a second inclined face extending from the bottom face.

\* \* \* \* \*